United States Patent [19]

Margulies

[11] Patent Number: 5,542,847
[45] Date of Patent: Aug. 6, 1996

[54] METHOD, APPARATUS AND DEVICE FOR DENTAL PROSTHESIS IMPLANTATION

[75] Inventor: Joseph Y. Margulies, 12 Long Pond Rd., Armonk, N.Y. 10504

[73] Assignees: Joseph Y. Margulies, Armonk; Avraham Kadar, Bedford, both of N.Y.

[21] Appl. No.: 303,438

[22] Filed: Sep. 9, 1994

[51] Int. Cl.⁶ .................................................. A61C 8/00
[52] U.S. Cl. ..................... 433/173; 433/174; 433/176
[58] Field of Search ................................. 433/173, 174, 433/175, 176

[56] References Cited

U.S. PATENT DOCUMENTS

| | | | |
|---|---|---|---|
| 2,745,180 | 5/1956 | Kiernan, Jr. | |
| 2,857,670 | 10/1958 | Kiernan, Jr. | |
| 3,981,079 | 9/1976 | Lenczycki | 433/174 |
| 4,044,466 | 8/1977 | Pasqualini et al. | 433/176 |
| 4,522,596 | 6/1985 | Ashkinazy | 433/173 |
| 4,732,564 | 3/1988 | Potucek et al. | 433/50 |
| 4,762,492 | 8/1988 | Nagai | 433/174 |
| 4,856,994 | 8/1989 | Lazzara et al. | 433/173 |
| 4,863,382 | 9/1989 | Bookstaber | 433/172 |
| 4,907,969 | 3/1990 | Ward | 433/173 |
| 5,013,242 | 5/1991 | Prezmecky | 433/173 |
| 5,106,299 | 4/1992 | Ghalili | 433/172 |
| 5,145,372 | 9/1992 | Daftary et al. | 433/173 |
| 5,297,963 | 3/1994 | Daftary | 433/172 |

OTHER PUBLICATIONS

Jean Solomon et al., "Kissing Dentures Goodbye", Newsweek, Mar. 9, 1992, p. 72.
Barnaby J. Feder, "Now, Implants Instead of Dentures", The New York Times, Oct. 9, 1993.
Steve Thurston, "Implants, The Teeth God Didn't Give You", American Health, Nov. 1988, p. 44.

*Primary Examiner*—Cary E. O'Connor
*Attorney, Agent, or Firm*—Helfgott & Karas. P.C.

[57] ABSTRACT

A dental implant, placed into a socket formed in the jaw bone, is held in position by screws that pass through the jaw bone from the buccal cortical surface to the lingual cortical surface, and through the implant that is located between the cortical surfaces. Threads on the screw shank form and engage threads in the cortex on opposite sides of the jaw bone. The implant, when inserted in the socket and anchored by the screws, is immediately strongly held to the jaw's bony structure. Stresses applied to a prosthetic device, e.g., a tooth crown that is attached to the implant, are substantially borne by the cortex by way of the screws.

28 Claims, 5 Drawing Sheets

METHOD, APPARATUS AND DEVICE FOR DENTAL PROSTHESIS IMPLANTATION

BACKGROUND OF THE INVENTION

This invention relates generally to a dental prosthesis that is attached to an implant embedded in the bone of a person's jaw, and more particularly to a method, apparatus and device for improving the attachment of the implant to the bone of the jaw and allowing for earlier loading.

Implantation of teeth in the mouth goes back to ancient times, being traced to the Pharaohs in Egypt. Because osseointegration techniques had not yet been discovered, attachments for these implants in the jaw bone were purely mechanical and were not as successful as the present techniques that rely on osseointegration. However, before osseointegration, it was not necessary to wait for prolonged time periods until integration was completed. U.S. Pat. Nos. 2,745,180 and 2,857,670, issued to Kiernan in 1956 and 1958, respectively, provide means for attachment of an implant to the jaw bone structure by means of pins that are forced laterally out from the implant after the implant is inserted in the bone. These pins have pointed ends that, with application of high force, penetrate the bony structure, i.e., the softer spongiosa of the jaw bone, in an effort to make a tooth implant permanent. However, the spongiosa is a relatively soft, living bony material, and subject to changes. Accordingly, reliability and permanence of an implant were not assured.

It is now common when it is desired or necessary to replace a missing tooth, to open the gum and to embed an implant in the bone structure beneath the gum. The implant is held in the bone in a socket hole by friction or the implant may be threaded into the bone. The gum is then closed over the implant and heals. When a proper material is used for the implant, e.g., titanium, the bone grows into the implant by osseointegration so that after several months the implant becomes a part of the bone structure in the mouth.

The procedures, which are followed after osseointegration has advanced, depends upon the dental practitioner's selection of a manufacturer's product. Many devices are available in complete systems of dental implants and prostheses for subsequent attachment to the implants. For example, a system that is widely used by dental practitioners is available from Nobelpharma USA Inc., Westmont, Ill.

In one system, the implant in a typical construction has an axially threaded hole at its top, i.e., the proximal end near the gum. After the bone has joined to the implant, the gum over the implant is reopened to expose the tapped hole. Then, an abutment is threaded into the tapped hole of the implant and extends to a level above the gum. The protruding end of the abutment is constructed with a non-round shape for attachment of a prosthesis. Also, the protruding end includes a central threaded hole extending inward toward the jaw bone.

A false tooth or crown is provided with a hole, known as a chimney, therethrough, and a non-round recess in its base that corresponds in shape to the protruding non-round cross-section of the abutment. Thereby, the crown can be joined to the abutment with a self-aligning connection that prevents relative rotation between them. A screw, passed into the chimney opening, engages the tapped hole in the abutment so as to hold the crown axially to the abutment. Thus, the crown cannot rotate about the abutment because it is fixed into the special contours on the exposed abutment end, and the crown cannot pull away from the abutment when the screw has been tightened in place.

Finally, the chimney above the screw is filled with a composite filler material that hardens and is shaped as part of the crown, to look like a natural tooth.

Such techniques have proven to be highly successful in a rapidly developing art. Implants have lasted ten and more years without replacement and the number of successful implants is in the order of 80%–90% of the implants undertaken. Failures most frequently occur when the implant fails to be properly integrated with the bony tissue of the jaw bone.

A major problem, and a source of patient dissatisfaction, resides in the several months of marked inconvenience for the patient while the process of osseointegration takes place and the implant becomes fixedly attached to the jaw bone. This difficulty, to be overcome, requires an avoidance of eating and chewing foods that will cause undesirable stresses and force transmissions in the tooth region. From present understanding, it appears that osseointegration takes place between the bone and the titanium implant under strict conditions of immobilization and without force or stress applied on the bone/implant interface. An uninterrupted growth of bone on the titanium surface is the time-consuming factor.

However, it is not completely clear at this time whether osseointegration taken place under the condition of extreme immobilization and, if not, how much movement of the implant is tolerable. It is also not clear whether controlled application of force is harmful, or may actually help if applied in a specific manner. From many years of metal implantation in bones, it has been learned that stress sharing constructions made of bone and implant encourage bone healing and bone growth, while stress shielding implants prevent healing, mainly by eliminating the stimuli from the body's osteoblasts.

After a tooth extraction, it is necessary that the site should heal prior to initiating implant procedures. This further extends the time period until the patient is ready to resume normal chewing at the site.

What is needed is an implant system that provides effective attachment to the bone in a shorter period of time than present implants require, and with less inconvenience for the patient during the period when osseointegration takes place.

SUMMARY OF THE INVENTION

It is an object of the invention to provide an improved method and apparatus for reducing the time period between the original implant procedures and completed installation of a permanent dental prosthetic device.

It is a further object of the invention to provide an improved dental implant that quickly provides a high strength connection between the jaw bone and the implant.

Another object of the invention is to provide and improve dental implant that provides increased strength in attachment of the finished prosthesis.

Yet another object of the invention is to provide an improved implant construction that is adaptable for use with existing commercial implant systems.

Still another object of the invention is to provide an improved implant construction that can be securely implanted as part of the same procedures with tooth extraction.

In accordance with the invention, a dental implant, placed into a socket formed in the jaw bone, is held in position by a screw or screws that pass through the jaw bone from one cortical surface to the opposite cortical surface (buccal to lingual), and through the implant that is located between the cortical surfaces. Threads on the ends of the screw shank form and engage threads in the cortex on opposite sides of the jaw bone. Thus, the implant when inserted in the socket and anchored by the screws, is immediately strongly held to the jaw's bony structure. Stresses that may be applied to any prosthetic device, such as a tooth crown, that is attached to the implant, are borne by the cortex, the strongest portions of the jaw bone, and not by the spongiosa within the jaw bone.

As soon as the gum, which was opened to allow insertion of the implant into the bone, has healed, the prosthesis can be completed and put to use, although the process of osseointegration is not yet complete. Thus, in a matter of weeks, as compared to three to six months in the prior art procedures, an implant may be in use.

Use of transverse screw fasteners in interlocking the implant in the jaw bone is based on the concept that eventually the implant is retained permanently by completed osseointegration. The screws provide a protected environment for osseointegration to occur, and provide the possibility to apply force on the implant and bone shortly after implantation is present. This construction may allow a patient to chew and eat as soon as the soft gum tissues are healed. Food that is of medium consistency, not hard or gummy, should be acceptable fare. In such a protected way, controlled stress application may even enhance the osseointegration process.

In some systems, the implants are provided with transverse holes through which the screws pass in attachment to the bone. Alternatively, the implants may be provided with lateral extensions that increase the surface area for contact where osseointegration can take place, and also provide paths through which and into which the attachment screws can be threaded. Thus, the screws may pass through a portion of the implant that is offset from the main implant body where other attachments are to be made, or the screws may pass directly through the implant center portion and through a central post that extends above the gum line and subsequently holds the tooth crown. In the latter construction, the screws hold the implant to the bone and also hold the main post in position in the implant.

At the time of installing an implant, a special aiming fixture is attached to the implant so that guide holes that are to be drilled through the jaw bone will automatically align with holes previously provided in the implant itself. The screws may be made of titanium or other materials. Biodegradable screws are known to be in the developmental stage and may prove useful in this application.

A combination of interlocking implants may be built by placing a plate on the outer aspect of the jaw and inserting the screws into the implants through the plate, which spans the distance between implants. Such jaw plates can be placed on both sides of the bone to provide an even more solid construction. An individual patient can have a combination of interlocked and regular implants in a manner where the structure above interlocked implants, e.g., temporary crowns, protects the regular individual implants from any stress or motion.

The invention accordingly comprises the several steps in the relation of one or more of said steps with respect to each of the others, the apparatus embodying features of construction, combinations and arrangements of parts which are adapted to effect such steps, and the article which possesses the characteristics, properties and relation of elements, all as exemplified in the detailed disclosure hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
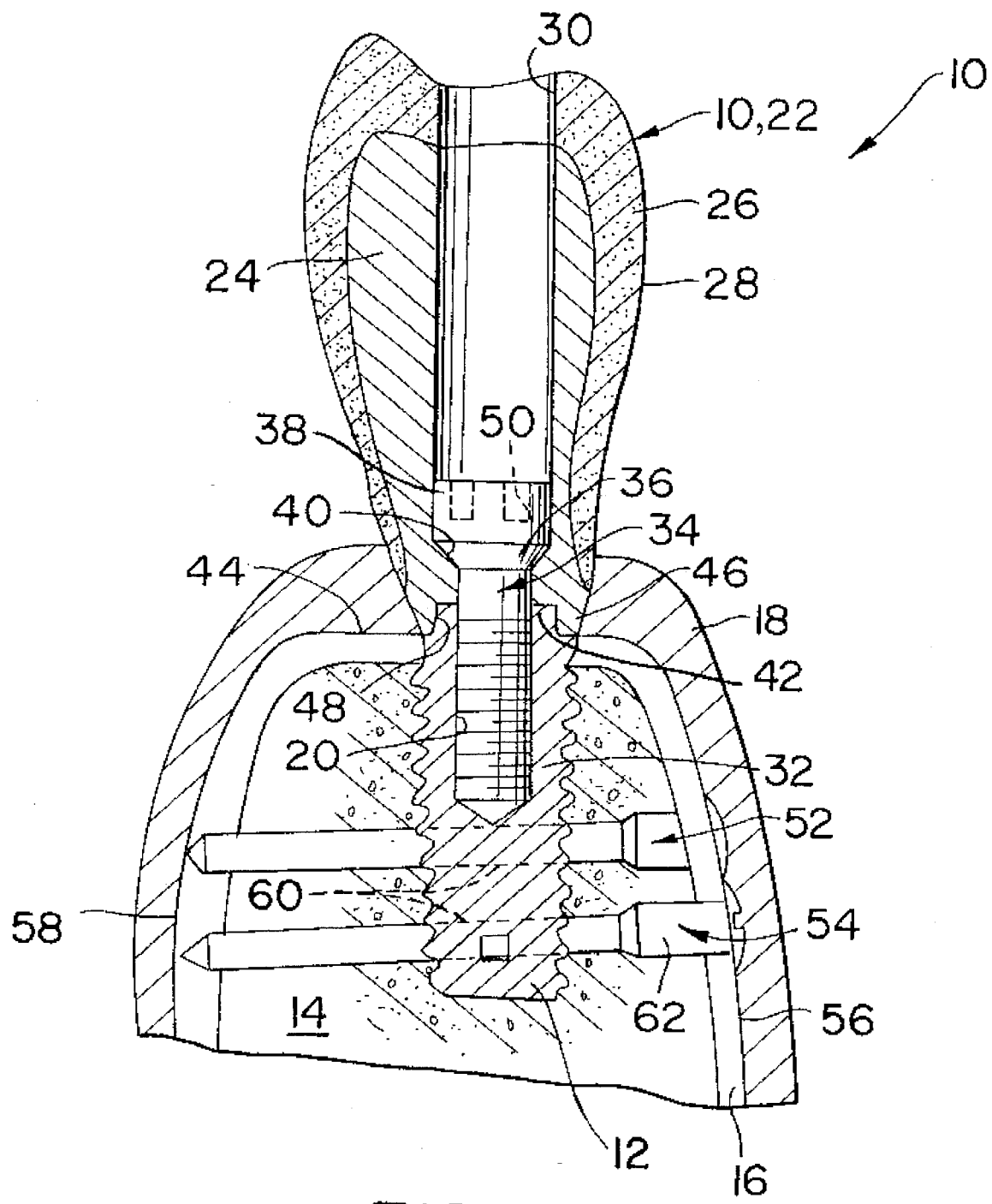
FIG. 1 is an elevational view in section of an attached implant in accordance with the invention and used in a conventional implant system of the prior art.

In FIG. 1, a dental prosthesis 10 in accordance with the invention, includes an implant 12 embedded in the spongiosa 14 of the jaw bone. After a healing period of several months, the implant 12 will become part of the bony structure by the process of osseointegration. The implant 12 protrudes through the cortex 16 of the jaw bone, and the gum tissue 18 has been parted to expose the proximal end of the implant 12, which has a tapped (threaded) hole 20 that opens and is accessible between the parted gum tissue 18. The crown 22 of a tooth is fitted in the opening of the gum tissue 18 and includes a central core 24 and an outer shell 26 that has an exterior surface 28 giving the appearance by color and texture of a natural tooth. A bore hole or chimney 30 in the crown 22 generally aligns with the tapped hole 20 in the implant 12.

A hexagonal boss 42 on the implant 12 protrudes above the surface 44 of the jaw bone cortex 16, and the base 46 of the crown 22 includes a hexagonal socket 48, whereby the crown 22 can be connected to the implant 12 with the implant boss 42 engaged in the hexagonal socket 48 of the prosthesis. Thereby, rotation of the crown 22 about the longitudinal axis of the screw 34 is prevented.

Threads 32 of a screw 34 engage the tapped hole 20. A bevel 36 on the screw head 38 engages a shoulder 40 at the base of the chimney 30 such that tightening the screw 34 into the threaded hole 20 of the implant 12 draws the crown 22 into a rigid connection with the implant 12 and consequently with the bony structure 14, 16 of the jaw.

In attaching the crown 22, the screw 34 is tightened by means of an Allen-head tool that engages the hexagonal socket 50 in the screw head 38. Then, the chimney 30 is filled with a filler material, known in the dental arts, and the working or biting surface of the filler material is contoured to match the remainder of the crown.

The construction described above is known in the art. The implant 12 may be screwed into the jaw bone or may be set into a prepared socket. When a titanium implant 12 is used, it is anticipated that the osseointegration process will bind the implant 12 permanently into the jaw after a period lasting three to six months.

In fabricating such an implant construction, the gum is parted; the socket for the implant is prepared, and the implant is set or threaded into place. Then, the gum opening is closed. The gum is allowed to heal, generally over a period of weeks and the osseointegration process is allowed to proceed, which process will take from three to six months. After osseointegration is complete, the gum tissue is again parted to provide access to the tapped hole 20 in the implant 12. Frequently, a gum shaping device or healing cap has been threaded into the tapped hole 20 and maintained in place while the gum heals after the initial implantation.

After the gum is opened the second time, the crown 22 is attached and the filler is applied to the chimney. Then, the gums must again be allowed to heal before the implant procedures are considered to be complete. During this entire period of time, the patient must favor the implant site to avoid movement of the implant and to avoid high stresses on the interface between the implant and the bony structure where osseointegration is expected to take effect.

To shorten this time period, in the embodiment, in accordance with the invention (FIG. 1), a pair of surgical screws 52, 54 extend from an outer side 56 (buccal) of the jaw bone to an inner side 58 (lingual) of the jaw bone. The screws are threadably engaged with the hard cortex layer 16 at both sides and pass through openings 60 in the implant 12, below the tapped hole 20. The screws 52, 54 are also threaded into the jaw bone spongiosa 14 but slide through the clearance holes 60 of the implant 12 at the time that the implant 12 is finally inserted into the jaw bone. Although the screws 52, 54 threadably engage the spongiosa 14 of the jaw bone, the stresses that may be applied to the prosthetic device 10 from whatever source, are borne primarily in the very strong, hard, unyielding, cortex layer 16 of the jaw bone. Because the danger has been substantially reduced that the implant 12 will loosen and move after the screws 52, 54 are applied and tightened into position, the prosthetic device 10 is ready for full service as soon as the gum tissue 18 has healed. In this way, the time which is required for bringing an artificial tooth into use, from initiation of the procedures until healing of the gums, is greatly shortened. The osseointegration process proceeds thereafter, but the prosthesis can be used while that process of osseointegration goes on.

The screws 52, 54 are self-tapping in the bone and may have cortical type threads, as are known in the medical arts, for tapping the cortex 16, and may have portions of threads that are most effective in tapping the spongiosa 14. The proximal screw portions 63, because they are the last portions to enter and engage the jaw bone, have a larger diameter than other portions of the screw shank so that a very tight engagement with the cortex 16 is made with the final turns of the screw.

As described above, the openings 60 through the implant 12 act as clearance holes for the surgical screws 52, 54. A snug fit is preferred at the openings 60 and the shank of the screws 52, 54 may provide an unthreaded portion so as to assure this snug fit.

Also, in alternative embodiments in accordance with the invention, the opening 60 may be threaded so as to engage mating threads on the screws 52, 54. In such a construction, the implant 12, can be brought into compressive contact, if desired, between the implant 12 and the spongiosa 14 as the screw 52 is tightened. As more is learned about the osseointegration process, it may be that such pressure is advantageous in enhancing integration beyond holding of the prosthetic device 10 in place, and ready for early use.

Also, if the openings 60 are threaded, the screws 52, 54 may be guided by openings in the cortex 16 and spongiosa 14 but may not be threadably engaged thereto.

Further, it should be understood that in alternative embodiments in accordance with the invention, the screws 52, 54 need not rest with their lead ends engaged in the cortex 16. The screws may terminate in the spongiosa 14. Also, the screws 52, 54, may be of reduced length so as to be supported only by the cortex 16 and spongiosa 14 on the right side (FIG. 1) of the jaw bone, with the ends of the screws 52, 54 not protruding from the left side of the implant 12. However, for the sake of strength and stability, it is preferred that the screws 52, 54 extend through both sides of the jaw bone, as illustrated.

Thus, attachment of the prosthetic device 10 to the hard cortical structure of the jaw bone, a primary object of the present invention, can be accomplished with transverse screws of many lengths and thread arrangements, so long as the stresses applied on the prosthetic device are at least in large part carried by the hard cortex 16 of the jaw bone. By this construction, the prosthetic device 10 can be placed into active use much earlier than implants of the prior art that rely solely on osseointegration, and with much greater effectiveness than in the Kiernan patents, mentioned above, where loads are borne by the relatively soft spongiosa of the jaw bone.

When the surgical screws 52, 54 are made of titanium, they may be left permanently in place so that they become part of the jaw bone by osseointegration. On the other hand, the screws 52, 54 may be later removed by opening the gums along-side the screw heads and thereby gaining access to the screw heads for removal of the screws. Additionally, biodegradable screws are in development and may provide advantage in use with prosthetic devices 10, as described.

Figure 2:
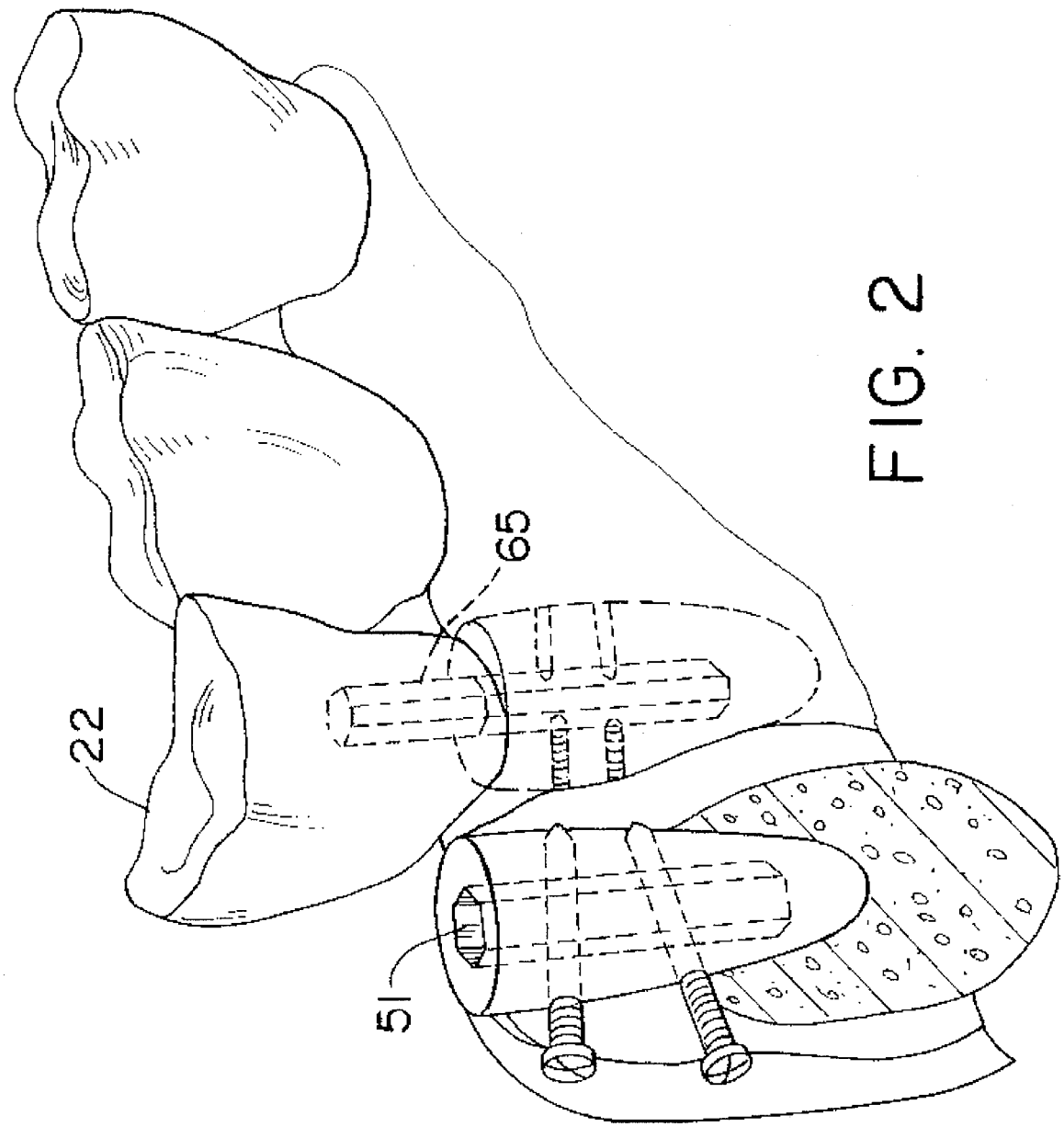
FIG. 2 is a top perspective view of an alternative implant in accordance with the invention, in a jaw bone.

The construction of FIG. 1 is based upon one type of implant. There are many implant systems on the market. For example, the threaded hole 20 of FIG. 1 may be replaced by a non-round socket 51, e.g., hexagonal (FIG. 2), into which a post 65 is inserted and attached. The crown 22 is later fixed to the post. Also, intermediate abutments (not shown) may be used between the implant 12 and the crown 22 so as to raise the region of attachment of the crown 22 to the implant 12 to a position above the gum line. Such an abutment is usually added after osseointegration has occurred and when the gum above the implant is opened for attachment of the crown.

Whereas, two surgical screws 52, 54 are illustrated in FIG. 1, it should be understood that in accordance with the invention, a single screw may serve, and more than two screws may also be used depending upon the location of attachment. Additionally, the location of the screws may in alternative embodiments in accordance with the invention, be changed.

For example, in FIG. 1, the screws 52, 54 do not interfere with the tapped hole 20 or screw 34. However, these screws can be moved closer to the crown 22 such that they pass through the screw 34. In this way, the screw 34 is prevented from backing out, a problem which sometimes occurs in the prior art. Also, the screw 34 can be of greater length so that the surgical screws 52, 54 are passed through the screw 34 after the screw 34 has been set into place.

Figure 4:
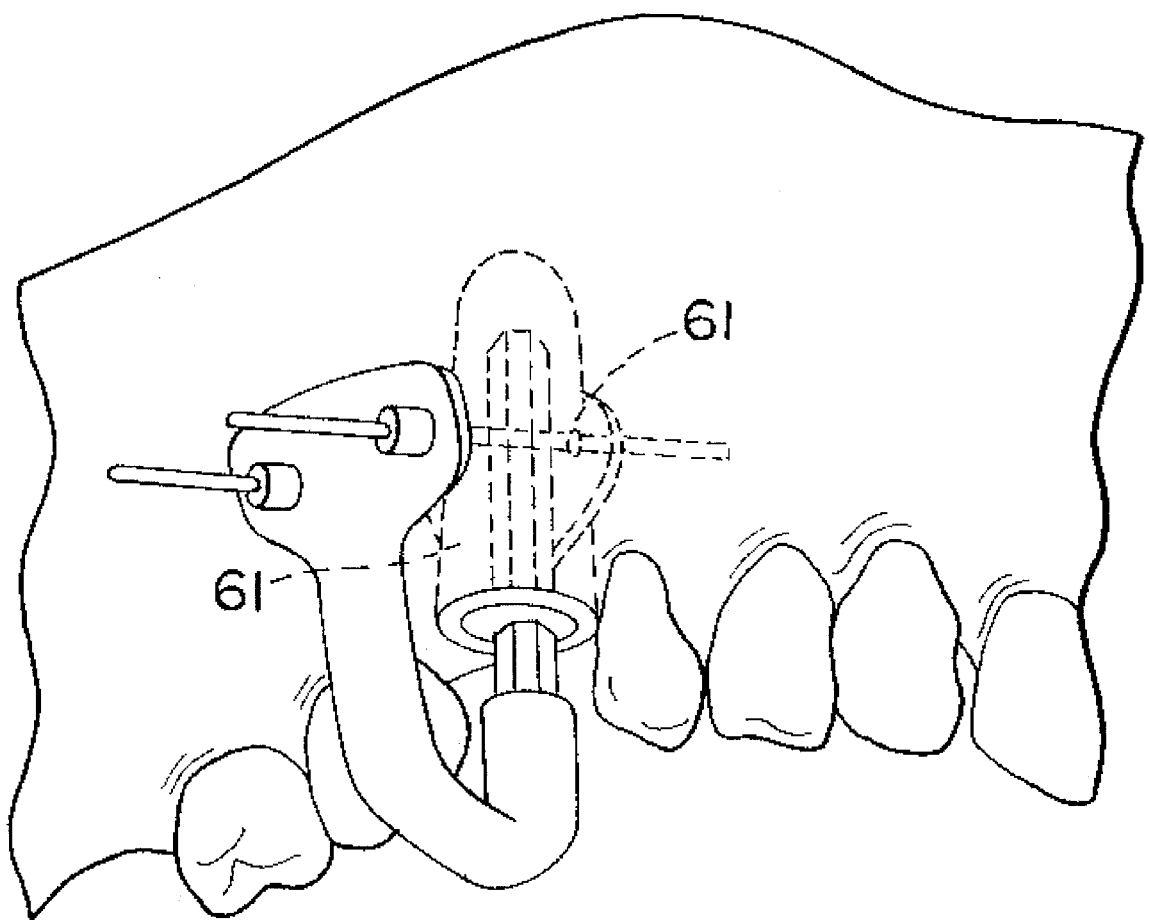
FIG. 4 is a bottom perspective view of another alternative implant in accordance with the invention.

Further, the surgical screws 52, 54 need not pass through the main body of the implant 12, as illustrated in FIG. 1. Lateral extensions or wings 61 may be provided (FIG. 4) on the implants. The opening for receiving an implant in the jaw bone would be modified to accommodate these lateral wings. Thus, such enlarged devices may be limited to use in the upper jaw bone where the bone structure is more massive. The surgical screws 52, 54, then pass through the jaw bone and also through the wings 61 where the screws form threads as they enter the material of the wings. In this regard, the thickness of the lateral wings can be selected for a strong, reliable joint with the selected screw threads. Additionally, the wings provide a greater surface in the jaw bone where osseointegration can take place. The overall result may be a stronger dental prosthesis.

Further, with reference to FIG. 1 as an example, the screws 52, 54 can extend beyond the surface at the inner side 58 of the jaw bone, and threaded machine nuts (not shown) can be placed onto the exposed screw ends and tightened. In such a construction, the surgical screw need not be threaded except at the very end and all holes including those in the jaw bone may be clearance holes.

For successfully embedding a prosthesis in the jaw bone and to assure a predictable implant procedure, it is necessary that the holes through the cortex 16 and spongiosa 14 be true and that they align accurately with holes 60 that are provided in the implant 12. Whether the screws pass through the main body of the implant or through lateral extensions from the implant, the screw hole alignment problem is always present and must be resolved. Also, experience with bone implants in other parts of the body indicates that it is necessary that a guide hole be provided through the bony structures before the screws 52, 54 are put in place in order to assure accuracy of alignment between the implant and the bony structure. Therefore, when performing an implantation, guide holes of very small diameter are first drilled through the jaw bone from the outer side 56 through to the inner side 58. The starting points for this drilling are laid open by cutting or piercing the adjacent gum tissue.

Figure 3:
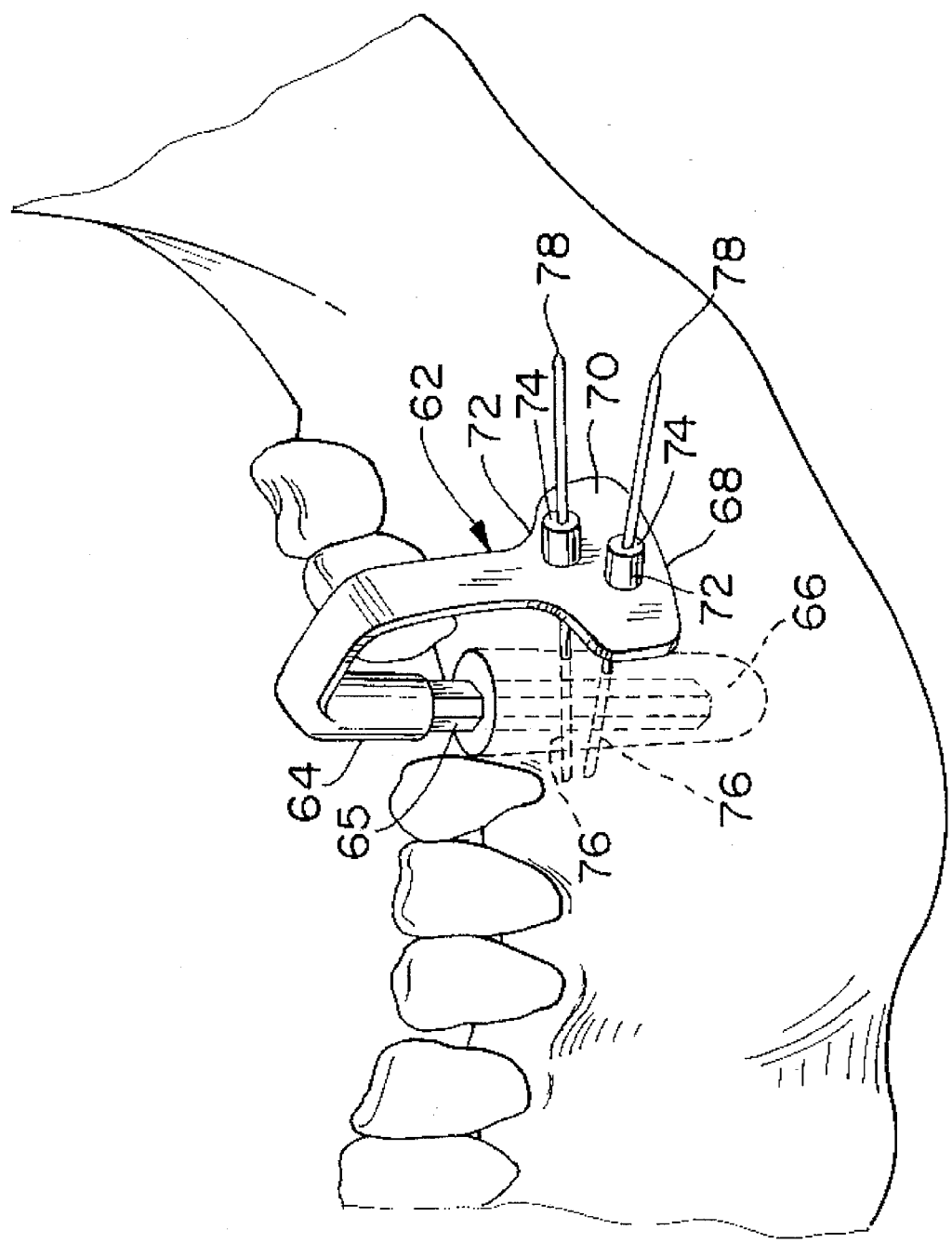
FIG. 3 is a top perspective view of the implant of FIG. 2 and an aiming device for locating screw holes in the jaw bone.

FIG. 3 shows an aiming tool 62 that is generally C-shaped. One end 64 of the tool 62 is adapted to mate with a post 65 extended from the implant 66. The post 65 is hexagonal in cross-section and the end 64 of the tool has a hexagonal socket, not visible in the drawing, so that, when assembled, the aiming tool 62, post 65 and implant 66 have fixed positions relative to each other. At the other end 68 of the tool 62, a plate 70 supports two bosses 72 that have guide holes 74 therethrough.

The implant 66 is manufactured to have through openings 76 that also pass through the post 65 in the embodiment of FIG. 3.

When the tool 62 is mounted to the post 65 and implant 66, the guide holes 74 in the tool and through openings 76 in the implant are in automatic alignment. This alignment can be verified before the implant is placed in the opened socket of the jaw bone. The post 65 is provided with clearance openings 76. The C-shape of the aiming tool 62, in combination with the implant 66, allows the implant to be positioned in its jaw socket and have the plate 70 rest against or be close to the outside of the jaw bone, as illustrated.

Then, using very fine guide drills 78, guide holes are produced that extend through the cortex 16 at the outer side 56, spongiosa 14, implant 12, spongiosa 14 and again the cortex 16 at the inner side 58. Then, the guide drills 78 are withdrawn, and the end 64 of the tool 62 is separated from the post 65. Surgical screws, e.g., similar to those in FIG. 1, are then driven through the guide holes and through the implant 12 to anchor the implant in the jaw bone. The surgical screws enlarge the guide holes 74 and tap these holes as the surgical screws progress through the jaw bone to produce a desired predetermined construction.

Alternatively, the holes formed by the guide drills can be tapped by a tapping tool and then screws are inserted.

The post 65 may then be used in attaching the remainder of the prosthetic device, e.g., the tooth crown, or an abutment to which the crown attaches, as discussed above. It should also be understood that the post 65 may be removed and replaced by a prosthetic element that has a hexagonal post extending therefrom.

Also, with regard to FIG. 1, as an example of a different implant construction, before setting the surgical screws 52, 54, the screw 34 is tightened into the implant 12, a supplemental hexagonal post is inserted in the socket 50 of the screw 34 and this post is used in conjunction with the tool 62. In this arrangement (FIG. 1), where the surgical screws 52, 54 do not pass through the central screw 34, it is possible to anchor the implant with the screws 52, 54, before the crown 22 is set in place.

As stated, depending upon the construction of the implant, the construction of the aiming tool can be varied such that accurate alignment is provided in preparing the guide holes through which the holding screws 52, 54 will be driven.

In accordance with the invention, a dental practitioner providing an implant for a patient follows these procedures. First, (using FIG. 1 as an example), the gum tissue 18 is opened and an opening or socket is prepared in the jaw bone. The selected implant is connected to a suitable aiming tool by inserting the screw 34 in the tapped opening 20 of the implant 12 and adding a hexagonal post (not shown) that seats in the socket 50 of the screw 34, and connects to the end 64 of the aiming tool 62. Then, the insert 12 is placed into the jaw socket with the plate 70 of the aiming tool 62 lying generally parallel to the outside surface of the jaw bone. It should be understood that if the implant 12 is to be screwed into a socket which was prepared in the jaw bone, then the sequence of steps will vary slightly in that the implant is first screwed into the jaw and then the screw 34 and hexagonal post may be added to aid in locating the guide holes for the screws.

The openings 74 on the aiming tool 62 and the openings 60 in the implant 12 have been checked for alignment prior to reaching this stage of the procedure. Then, using very fine drill bits, the guide holes are drilled, aligned by the bosses 72, through the jaw bone from the outer side to the inner side, the drills passing through the openings 60 in the implant 12 during the drilling step. After these guide holes have been completed, the guide drills 78 are withdrawn; the aiming tool 62 is removed along with any intermediate post 65 that is not intended to be a permanent part of the implant. Then, the surgical screws are driven through the guide holes to produce a construction as in FIG. 1, where the surgical screws, 52, 54 are supported by the cortex layers 16 of the jaw bone as well as the softer internal spongiosa 14.

The crown 22 and any intermediate elements (not shown) can then be added, after which the gums are treated and allowed to heal. Opening and closing of the gum tissues for insertion of the implant or for drilling or tapping holes for the surgical and guide screws, are techniques that are not novel portions of the present invention, and accordingly are not described in detail herein. Those skilled in the dental arts will have no difficulty in recognizing and practising the necessary procedures related to handling and treatment of the gum tissues.

Following these procedures, although osseointegration is perhaps not even started, the implant is ready for active use by the patient as soon as the gum tissues have healed. By relying on the cortex as the main rigid support, a strong, reliable, connection has been made ab initio between the implant and the jaw bone.

Figure 5:
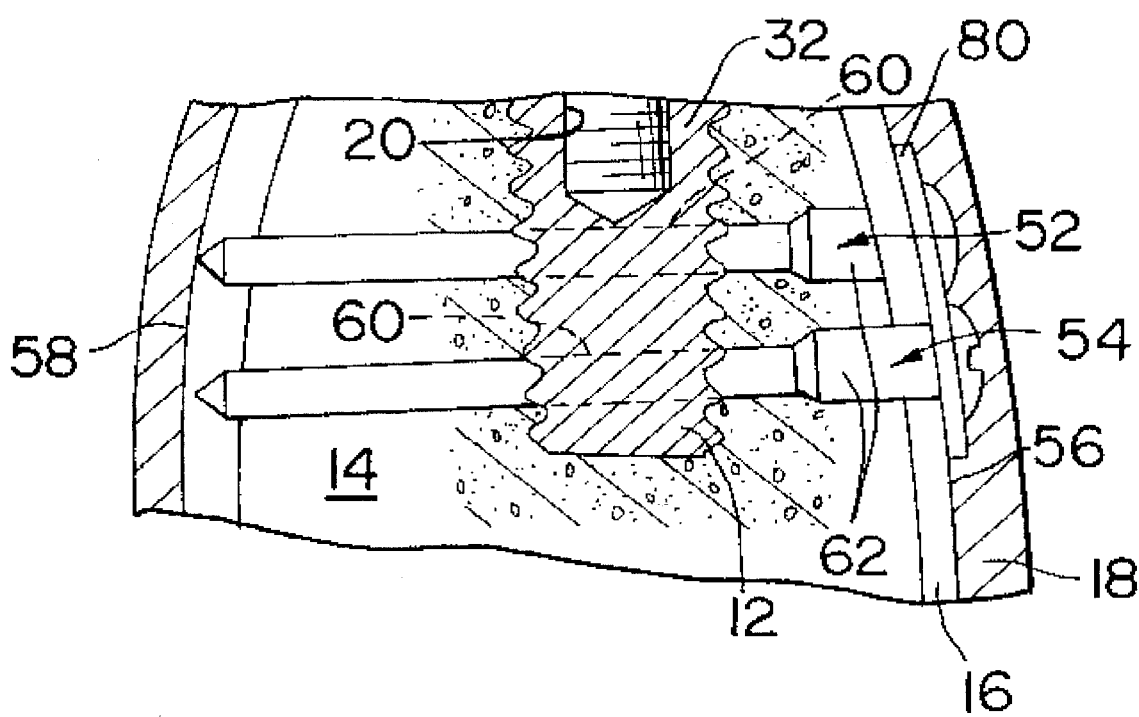
FIG. 5 is a fragmentary view in section and elevation similar to FIG. 1 of an alternative embodiment in accordance with the invention.

In an alternative embodiment (FIG. 5) in accordance with the invention, a thin plate 80, e.g. of titanium alloy, stainless steel or a biodegradable material, is placed beneath the heads of the screws 52, 54 and extends to other implants (not shown) that are, e.g., the next tooth or several teeth away. Thus, a firm structure is made between several implants to which other prosthetic devices, temporary or permanent, and other implants may be attached to make a solid construct. The plate 80 may also be used at a single implant to spread the stresses applied by the screw heads when they are tightened at the final position. Plates may be attached on either or both sides of the jaw bone. The gum tissue must be appropriately opened and closed to accommodate use of the plate 80.

It should also be understood that in some instances the screws 52, 54 may be inserted into the jaw bone from the lingual side, at the discretion of the practitioner, in accordance with the method of the invention.

In further alternative embodiments in accordance with the invention, the screws 52, 54 may be replaced with pins or rivets that are frictionally engaged in transverse holes. Such devices may have a fixed head at one end and be expanded at the other end after passing through the jaw bone so that once inserted they remain in place until removed (or degraded where biodegradable materials are used). Wire and cable systems, as used in orthopedic surgery, may also be applied. Any means that immediately secures the desired position of the implant in a jaw bone socket by mechanical interengagement with the cortical surfaces of the jaw bone and permits early application of forces on the implant, is intended to fall within the scope of the invention.

It will thus be seen that the objects set forth, among those made apparent from the preceding description, are efficiently attained and, since certain changes may be made in carrying out the above method, in the described product, and in the construction set forth without departing from the spirit and scope of the invention, it is intended that all matter contained in the above description and shown in the accompanying drawings shall be interpreted as illustrative and not in a limiting sense.

What is claimed is:

1. A method for installation in the jaw bone of a patient of a dental prosthesis including an implant, comprising the steps:
   (a) providing an opening in the gum at the intended site of implantation;
   (b) forming a socket to receive said implant in the jaw bone at the opened site;
   (c) inserting said implant in said socket;
   (d) positioning at least one support plate on at least one of a buccal side and lingual side of said jaw bone;
   (e) passing at least one screw through said at least one support plate, said at least one support plate being retained against said jaw bone by said screw, and at least partially through said jaw bone and implant, said screw holding said implant in said jaw bone socket.

2. A method as in claim 1, wherein said implant includes a central opening and interface means for engaging a prosthetic tooth element, said at least one screw being transverse to a longitudinal axis of said central opening.

3. A method as in claim 2, wherein said at least one screw one of passes transversely through said central opening and bypasses said central opening.

4. A method as in claim 2, wherein said implant preceding step (c) includes at least one transverse hole for passage therethrough of said at least one screw, further comprising, following step (b), the substeps:
   (i) removably connecting an aiming tool to said implant, said aiming tool, when connected, having a first end making the connection to said implant, a tool plate at a second end of said tool, and a bend between said ends, said tool plate having at least one guide hole therethrough with a longitudinal axis aligned to said at least one transverse hole in said implant, said at least one screw in step (e) passing through said at least one transverse hole;
   (ii) positioning said tool plate against a surface of said support plate when said implant and support plate are inserted in step (c) and step (d);
   (iii) boring at least one hole through said jaw bone by drilling through, and in alignment with, said tool plate guide hole;
   (iv) removing said aiming tool from said implant and said jaw bone,
   said at least one screw of step (e) passing through said bored hole of substep (iii).

5. A method as in claim 1, wherein said at least one screw is a threaded surgical screw that taps mating threads in said jaw bone as said screw enters.

6. A method as in claim 5, wherein said at least one screw is threadably engaged with a cortex layer of said jaw bone.

7. A method as in claim 6, wherein said at least one screw is further threadably engaged with spongiosa of said jaw bone.

8. A method as in claim 6, wherein said at least one screw extends through the buccal side and the lingual side of the jaw bone.

9. A method as in claim 1, wherein said implant includes a main body and at least one lateral extension from said main body, said at least one screw passing through and engaging said at least one extension.

10. A method as in claim 9, wherein said at least one extension and said at least one screw are threadably engaged.

11. A method as in claim 1, wherein in step (e) said screw passes from one of an inner lingual surface and an outer buccal surface at least partially through said jaw bone and said implant.

12. A dental prosthesis, comprising:
    an implant for insertion in a first direction into a socket formed in a jaw bone where a natural tooth is absent, said implant having an axis oriented in said first direction, engagement means at one end for joining to a prosthetic tooth element, and at least one screw hole through said implant in a second direction transverse to said first direction at a location to be within said jaw bone after implantation;
    at least one surgical screw having a diameter for passing through said at least one screw hole, said screw having a fit in said screw hole to limit motion therebetween; and
    at least one support plate for positioning against at least one cortical surface of said jaw bone, said at least one screw, in use, passing through said at least one plate and through said at least one screw hole in said implant to hold said at least one plate against said jaw bone in fixed relationship to said implant.

13. A dental prosthesis as in claim 12, wherein said at least one screw has a length to extend through the jaw bone from a buccal side to a lingual side.

14. A dental prosthesis as in claim 13, wherein said at least one screw has a lead end and a screw head end and is threaded at least at its lead end and adjacent said screw head end so as to threadably engage said buccal and lingual sides of said jaw bone.

15. A dental prosthesis as in claim 14, wherein said at least one screw is self-tapping.

16. A dental prosthesis as in claim 13, wherein said screw is threaded and having a threaded engagement within said screw hole in said implant.

17. A dental prosthesis as in claim 13, wherein said screw is unthreaded and having a sliding fit within said screw hole in said implant.

18. A dental prosthesis comprising:

an implant for insertion in a first direction into a socket formed in a jaw bone where a natural tooth is absent, said implant having an axis oriented in said first direction, engagement means at one end for joining to a prosthetic tooth element, and at least one screw hole through said implant in a second direction transverse to said first direction at a location to be within said jaw bone after implantation;

at least one surgical screw having a diameter for passing through said at least one screw hole, said screw having a fit in said screw hole to limit motion therebetween, said at least one screw having a length to extend through the jaw bone from a buccal side to a lingual side, and having a lead end and a screw head end and being threaded at its lead end and adjacent said screw head end so as to threadably engage said buccal and lingual sides of said jaw bone, said threads at said lead end have a smaller diameter than said threads at said screw head end.

19. A dental prosthesis as in claim 18, wherein said at least one screw is self-tapping.

20. A dental prosthesis as in claim 18, wherein said screw is threaded and having a threaded engagement within said screw hole in said implant.

21. A dental prosthesis as in claim 18, wherein said screw is unthreaded and having a sliding fit within said screw hole in said implant.

22. A method for installation in the jaw bone of a patient of a dental prosthesis including an implant, comprising the steps:

(a) providing an opening in the gum at the intended site of implantation;

(b) forming a socket to receive said implant in the jaw bone at the opened site;

(c) inserting said implant in said socket;

(d) positioning at least one support plate on at least one of a buccal side and lingual side of said jaw bone; and (e) passing at least one fastening means through said at least one support plate, said at least one support plate being retained against said jaw bone by said fastening means, and at least partially through said jaw bone and said implant, said fastening means holding said implant in said jaw bone socket.

23. A method as in claim 22 wherein said implant includes a central opening and interface means for engaging a prosthetic tooth element, said at least one fastening means extending transversely to a longitudinal axis of said central opening.

24. A method as in claim 22, wherein said at least one fastening means is one of a group consisting of a screw rivet, pin, cable, and wire.

25. A method as in claim 24, wherein said at least one fastening means is supportably engaged with a cortex layer of said jaw bone.

26. A dental prosthesis, comprising:

an implant for insertion in a first direction into a socket formed in a jaw bone where a natural tooth is absent, said implant having an axis oriented in said first direction, engagement means at one end for joining to a prosthetic tooth element, and at least one hole through said implant in a second direction transverse to said first direction at a location to be within said jaw bone after implantation;

at least one fastening means having a cross section for passing through said at least one hole, said fastening means having a fit in said hole for limiting motion therebetween and for holding said implant in said jaw bone; and at least one support plate for positioning against at least one cortical surface of said jaw bone, said at least one fastening means, in use, passing through said at least one support plate and through said at least one hole in said implant to hold said at least one support plate against said jaw bone in fixed relationship to said implant.

27. A dental prosthesis as in claim 25, wherein said at least one fastening means extends through the jaw bone from a buccal side to a lingual side.

28. A dental prosthesis as in claim 26, wherein said fastening means is one of a group consisting of a screw, rivet, pin, cable and wire.

* * * * *